United States Patent
Stampanoni et al.

(10) Patent No.: US 9,439,615 B2
(45) Date of Patent: Sep. 13, 2016

(54) SYSTEM FOR NON-INVASIVE CLASSIFICATION OF DIFFERENT TYPES OF MICRO-CALCIFICATIONS IN HUMAN TISSUE

(71) Applicant: PAUL SCHERRER INSTITUT, Villigen PSI (CH)

(72) Inventors: Marco Stampanoni, Endingen (CH); Zhentian Wang, Brugg (CH)

(73) Assignee: Paul Scherrer Institut, Villigen (CH)

(*) Notice: Subject to any disclaimer, the term of this patent is extended or adjusted under 35 U.S.C. 154(b) by 194 days.

(21) Appl. No.: 14/380,817

(22) PCT Filed: Feb. 7, 2013

(86) PCT No.: PCT/EP2013/052451
§ 371 (c)(1),
(2) Date: Aug. 25, 2014

(87) PCT Pub. No.: WO2013/124164
PCT Pub. Date: Aug. 29, 2013

(65) Prior Publication Data
US 2015/0030123 A1 Jan. 29, 2015

(30) Foreign Application Priority Data
Feb. 24, 2012 (EP) .................................... 12156853

(51) Int. Cl.
*A61B 6/04* (2006.01)
*A61B 6/00* (2006.01)
(Continued)

(52) U.S. Cl.
CPC ............. *A61B 6/502* (2013.01); *A61B 6/4035* (2013.01); *A61B 6/4291* (2013.01); *A61B 6/483* (2013.01);
(Continued)

(58) Field of Classification Search
CPC ...... A61B 6/502; A61B 6/483; A61B 6/484; A61B 6/4035; A61B 6/4291; G06T 7/0012; G06T 11/005; G06T 2207/10081; G06T 2211/40

USPC ..................................... 378/37; 382/128–132
See application file for complete search history.

(56) References Cited

U.S. PATENT DOCUMENTS 5,999,639 A * 12/1999 Rogers ..................... B25J 15/04
  382/132
2012/0041679 A1 2/2012 Stampanoni et al.
(Continued)

FOREIGN PATENT DOCUMENTS

CN 1273516 A 11/2000
CN 101234026 A 8/2008
(Continued)

OTHER PUBLICATIONS

Frappart et al: "Different types of microcalcifications observed in breast pathology", Virchows Archiv Für Pathologische Anatomie Und Physiologie Und Für Klinische Medizin, Berlin, Springer, DE, vol. 410, No. 3, Jan. 1, 1987, pp. 179-187, XP009155233, ISSN: 0376-0081, DOI: 10.1007/BF00710823.
(Continued)

*Primary Examiner* — Courtney Thomas
(74) *Attorney, Agent, or Firm* — Laurence Greenberg; Werner Stemer; Ralph Locher

(57) ABSTRACT

A non-invasive method distinguishes between two types of micro-calcification by x-ray imaging in mammography. Two major types of micro-calcifications are found and confirmed by histopathology and they are correlated to benign and malignant breast lesions. Distinguishing between them non-invasively will significantly improve early breast cancer diagnosis. This is based on the fact that these two types of micro-calcifications show opposite absorption and small-angle scattering signals in x-ray imaging. The imaging system, which can record these two signals of the breast tissue simultaneously for instance, an x-ray grating interferometer, can be used to uniquely determine the micro-calcification type. This is expected to be used in mammography to improve early breast cancer diagnosis, increase diagnosis accuracy and decrease the biopsy rate.

12 Claims, 1 Drawing Sheet

(51) Int. Cl.
*G06T 7/00* (2006.01)
*G06T 11/00* (2006.01)

(52) U.S. Cl.
CPC ............ *A61B 6/484* (2013.01); *A61B 6/5217* (2013.01); *G06T 7/0012* (2013.01); *G06T 7/0097* (2013.01); *G06T 11/005* (2013.01); *G06T 2207/10081* (2013.01); *G06T 2207/10116* (2013.01); *G06T 2207/20212* (2013.01); *G06T 2207/30068* (2013.01); *G06T 2211/40* (2013.01)

(56) References Cited

U.S. PATENT DOCUMENTS

2014/0010344 A1* 1/2014 Nagatsuka ............... A61B 6/06
378/37
2014/0112440 A1 4/2014 David et al.

FOREIGN PATENT DOCUMENTS

WO 2010059319 A1 8/2010
WO 2012000694 A1 1/2012

OTHER PUBLICATIONS

Pfeiffer et al: "Hard-X-ray dark-field imaging using a grating interferometer", Nature Materials, vol. 7, No. 2, Feb. 1, 2008, pp. 134-137, XP055003146, ISSN: 1476-1122, DOI: 10.1038/nmat2096.

Weitkamp et al: "Tomography with grating interferometers at low-brilliance sources", Proceedings of SPIE, vol. 6318, Aug. 31, 2006, p. 63180S, XP055060370, ISSN: 0277-786X, DOI: 10.1117/12.683851.

Foschini et al: "Microcalcifications in ductal carcinoma in situ of the breast: Histochemical and immunohistochemical study", Human Pathology, vol. 27, No. 2, Feb. 1, 1996, pp. 178-183, XP055060193, ISSN: 0046-8177, DOI: 10.1016/S0046-8177(96)90372-X.

Stampanoni et al: "The First Analysis and Clinical Evaluation of Native Breast Tissue Using Differential Phase-Contrast Mammography", Investigative Radiology, Lippincott Williams & Wilkins, US, vol. 46, No. 12, Dec. 1, 2011, pp. 801-806, XP009155431, ISSN: 0020-9996, DOI: 10.1097/RLI.0B013E31822A585F.

Chapman et al: "Diffraction Enhanced X-Ray Imaging", Physics in Medicine and Biology, Institute of Physics Publishing, Bristol GB, vol. 42, No. 11, Nov. 1, 1997, pp. 2015-2025, XP000720152, ISSN: 0031-9155, DOI: 10.1088/0031-9155/42/11/001.

Miklos Z Kiss et al: "Improved image contrast of calcifications in breast tissue specimens using diffraction enhanced imaging; Improved image contrast of calcifications in breast tissue specimens using diffraction enhanced imaging", Physics in Medicine and Biology, Institute of Physics Publishing, Bristol GB, vol. 49, No. 15, Aug. 7, 2004, pp. 3427-3439, XP020023822, ISSN: 0031-9155.

Olivo A et al: "Image formation principles in coded-aperture based x-ray phase contrast imaging", Physics in Medicine and Biology, Institute of Physics Publishing, Bristol GB, vol. 53, No. 22, Nov. 21, 2008, pp. 6461-6474, XP020141513, ISSN: 0031-9155, DOI: 10.1088/0031-9155/53/22/012.

Pfeiffer et al: "Phase retrieval and differential phase-contrast imaging with low-brilliance X-ray sources", Nature Physics, Nature Publishing Group, London, GB, vol. 2, Mar. 26, 2006, pp. 258-261, XP002518081, ISSN: 1745-2473, DOI: 10.1038/NPHYS265 [retrieved on Mar. 5, 2009].

Wang Zhen-Tian et al: "Quantitative grating-based x-ray dark-field computed tomography", Applied Physics Letters, AIP, American Institute of Physics, Melville, NY, US, vol. 95, No. 9, Sep. 3, 2009, pp. 94105-94105, XP012122950, ISSN: 0003-6951, DOI: 10.1063/1.3213557.

Fan Quing-fu, "New Development of Diagnosis and Treatment Technology of Breast Cancer", Shangai Biomedical Engineering, vol. 25, No. 2, Jun. 30, 2004, pp. 56-61—Statement of Relevance.

Vieng De-gang et al., "Applications of Synchrotron Radiation in Medical Imaging", Chinese Journal of Medical Physics, vol. 26, No. 4, Jul. 31, 2009, pp. 1277-1280—English abstract.

\* cited by examiner

SYSTEM FOR NON-INVASIVE CLASSIFICATION OF DIFFERENT TYPES OF MICRO-CALCIFICATIONS IN HUMAN TISSUE

BACKGROUND OF THE INVENTION

Field of the Invention

The present invention relates to a system for non-invasively classification of different types of micro-calcifications in human tissue.

Breast cancer is the most common cancer in women and the 2nd leading cause of cancer deaths. International standards for diagnostics and treatment are not stringently followed and it is estimated that 35% of all breast cancer deaths in Europe could be avoided if optimal diagnostic and therapeutic procedures would always be applied.

The current golden standard for mammography is absorption-based x-ray imaging. The presence of micro-calcifications on the mammogram is an important feature of particular diagnostic significance. Two major types of micro-calcifications are found in breast tissue and they are thought to correlate with benign and malignant breast lesions. Type I micro-calcifications consist of calcium oxalate dehydrate ($CaC_2O_4 \cdot 2H_2O$) and type II are composed of calcium phosphates, mainly calcium hydroxyapatite ($Ca_5(PO_4)_3(OH)$). Pathology studies using light microscopy show that type I micro-calcifications are amber, light yellow, partially transparent and have a crystal structure which presents birefringent characteristics under polarized light. Type II micro-calcifications are noncrystalline, generally ovoid or fusiform, gray-white, and non-birefringent under polarized light.

Type I micro-calcifications are seen most frequently in benign ductal cysts and are rarely found in foci of carcinoma, whereas Type II are most often seen in proliferative lesions, including carcinomas. It has been confirmed that the presence of type I micro-calcifications is a strong indication that a lesion is benign or, at most, an in situ lobular carcinoma. Thus, distinguishing their types is very helpful to discern the characteristics of breast lesions and furthermore improve breast cancer early diagnosis. If this distinction can be determined in the breast imaging stage, biopsy rates will be decreased.

Efforts have been made to distinguish these two types of micro-calcifications by various methods. These methods can be divided into invasive and noninvasive methods. Noninvasive methods try to achieve this goal by analyzing conventional mammograms. They attempt to correlate morphological parameters such as the shape, size, number, and roughness of mammographically detected micro-calcifications. These algorithms bear problems such as dark mammographic background, low density calcific flecks, or densely clustered calcifications. Moreover, morphological information is not specific and therefore their algorithms are limited to certain patients and mammograms and are found not to be reliable in clinical diagnosis.

A more rigorous method is the use of Raman spectroscopy. Raman spectroscopy is a technique based on the exchange of energy between light and matter. Raman spectra obtained are chemical specific, and therefore this technique is able to determine the micro-calcification types. Their results show that this method leads to a sensitivity of 88% and a specificity of 93% in distinguishing micro-calcifications occurring in benign and malignant ducts.

The methods based on the mammogram are noninvasive and clinically applicable, but the reliability is low. This can be understood because these methods cannot determine the chemical compositions or the structure of the micro-calcifications by only the x-ray absorption information. Morphological information is limited by various individual patients and the environment of the foci of infections. The Raman spectroscopy has a higher sensitivity and specificity. However, it is an invasive method. Ex-vivo specimens must be prepared for analyzing which limits its applications in early diagnosis.

Another reliable method is histopathology, such as H&E (hematoxylin and eosin) stains with light microscopy. These two types of micro-calcifications show different birefringent properties under polarized light: Type I is found to be birefringent while type II is non-birefringent. However, this pathology method is also invasive and therefore shares the same disadvantages as the method based on Raman spectroscopy.

BRIEF SUMMARY OF THE INVENTION

It is therefore an objective of the present invention to provide a system for non-invasively classification of different types of micro-calcifications in human tissue which is capable of distinguishing these two types of micro-calcifications in the breast imaging stage, and is able to provide information that reflects the internal chemical or structures of the micro-calcification, not only morphological information.

This objective is achieved according to the present invention by a system for non-invasively classification of different types of micro-calcifications in human tissue by combining their absorption and small-angle scattering signals; said system comprising:
a) a set-up for recording absorption and small-angle scattering signals, such as X-ray investigations based on grating-based interferometry or on analyzer-crystal-based imaging or on coded aperture imaging;
b) a signal processing means being enabled to analyse at least one pair of micro-calcifications, said analysis being based on the finding that different types of micro-calcifications have opposite absorption and small-angle scattering signals, that is, one type gives a weaker absorption signal but a stronger small-angle scattering signal than the other type or vice-versa.

The present system therefore benefits from the fact that these two types of (micro)-calcifications show opposite absorption and small-angle scattering signals in x-ray imaging. The imaging system which records these two signals of the breast tissue simultaneously (for instance, an x-ray grating interferometer according to WO 2012/000694 A1 or WO 2010/089319 A1), is used to uniquely determine the micro-calcification type. The present invention is used in mammography to improve early breast cancer diagnosis, increase diagnosis accuracy and decrease the biopsy rate.

The system comprises in a preferred embodiment that the signal processing means are enabled to assign a signal pair $(t_1, t_2)$ to a pair of micro-calcifications; $t_1, t_2 \subset \{+, -\}$ and $t_1$ and $t_2$ represent the relative signal strength of the absorption and small angle scattering signals, respectively, wherein "+" means this signal is stronger, "−" means this signals is weaker; and an evaluator module comprised in the signal processing means identifies if two signal pairs constitute a combination of (+,−) and (+,−), which yields that the two signal pairs belong to different types of micro-calcifications wherein a micro-calcification signed to (−,+) is determined to be more likely a type I micro-calcification whereas (+,−) indicates that this micro-calcification is determined to be more likely a type II micro-calcification.

In order to broaden the capabilities of the present system with respect to the accuracy and robustness, a preferred embodiment enables the data processing means to use the ratio r of the absorption signal and the small-angle scattering signal of the micro-calcification to decouple the thickness parameter and identify micro-calcification types I and II, wherein $$r = \frac{AC}{SC}$$
$$= \frac{\bar{\mu} \cdot L}{c\bar{S} \cdot L}$$
$$= \frac{\bar{\mu}}{c\bar{S}},$$

AC is the absorption signal, $AC = \int_0^L \mu(l) dl = \bar{\mu} \cdot L$ and SC is the small-angle scattering signal, $SC = c \int_0^L S(l) dl = c\bar{S} \square L$; with L is the thickness of the specimen, $\mu$ is the attenuation coefficient, S is the generalized scattering parameter, and c is a constant decided by the geometry and system parameters of the set-up; further using an predetermined threshold t that will sort out if, $$\begin{cases} r < t, \text{ one type} \\ r > t, \text{ another type} \end{cases}.$$

Another preferred embodiment may provided for a system, wherein—provided that the signal data is obtained with (multi-modality) computed tomography—the data processing means are reconstructing the tomograms of the absorption signals and the scattering signals from their projection and the attenuation coefficient $\mu$ and the general scattering parameter S are obtained directly, wherein these two signals are also opposite for two types of micro-calcifications.

With respect to the set-up, a further preferred embodiment provides for a X-ray interferometer setup, where the absorption signals and the small-angle scattering signals are obtained from an arrangement for x-rays, in particular hard x-rays, for obtaining quantitative x-ray images from a sample including:
  a. an X-ray source;
  b. three or at least two gratings named G0, G1 and G2 or G1 and G2,
  c. a position-sensitive detector with spatially modulated detection sensitivity having a number of individual pixels;
  d. means for recording the images of the detector,
  e. the evaluator module being enabled to evaluate the intensities for each pixel in a series of images, in order to identify the characteristics of the object for each individual pixel as an absorption dominated pixel or a differential phase contrast dominated pixel or an x-ray scattering dominated pixel;
  f. wherein the series of images is collected by continuously or stepwise rotating from 0 to $\pi$ or $2\pi$ either the sample or the setup and the source relative to the sample.

Preferably, the afore-mentioned setup may be operated either in the so-called "near field regime" or in the "Talbot-regime".

Preferred details of the X-ray interferometer setup are given below. The grating G1 can be a line grating being either an absorption grating or a phase grating which is a low absorption grating but generating a considerable X-ray phase shift, the latter preferably of $\pi$ or odd multiples thereof; and the grating G2 is a line grating having a high X-ray absorption contrast with its period being the same as that of the self image of the grating G1; the grating G2 is placed closely in front of the detector with its lines parallel to those of the grating G1.

For near-field-regime operation, the distance between the gratings may be chosen freely within the regime, and for the Talbot-regime may be chosen according to $$D_{n,sph} = \frac{L \cdot D_n}{L - D_n}$$
$$= \frac{L \cdot n \cdot p_1^2 / 2\eta^2 \lambda}{L - n \cdot p_1^2 / 2\eta^2 \lambda}$$

where n=1, 3, 5 . . . , and $$\eta = \begin{cases} 1 & \text{if the phase shift of } G_1 \text{ is } (2l-1)\frac{\pi}{2}, \quad p_2 = \frac{L + D_{n,psh}}{L} p_1 \\ 2 & \text{if the phase shift of } G_1 \text{ is } (2l-1)\pi, \quad p_2 = \frac{L + D_{n,psh}}{L} \frac{p_1}{2} \end{cases},$$

where l=1, 2, 3, . . . , $D_n$ is an odd fractional Talbot distance when a parallel X-ray beam is used, while $D_{n,sph}$ is that when the fan or cone X-ray beam is used, L is the distance between the X-ray source and the grating G1.

The afore-mentioned X-ray interferometer setup can be used in the phase stepping approach, wherein the phase stepping can be performed by the shift of one grating G0, G1 or G2 with respect to the others.

Preferred embodiments of the present invention are hereinafter explained in more detail with respect to the following drawings:

DESCRIPTION OF THE INVENTION

Figure 1:
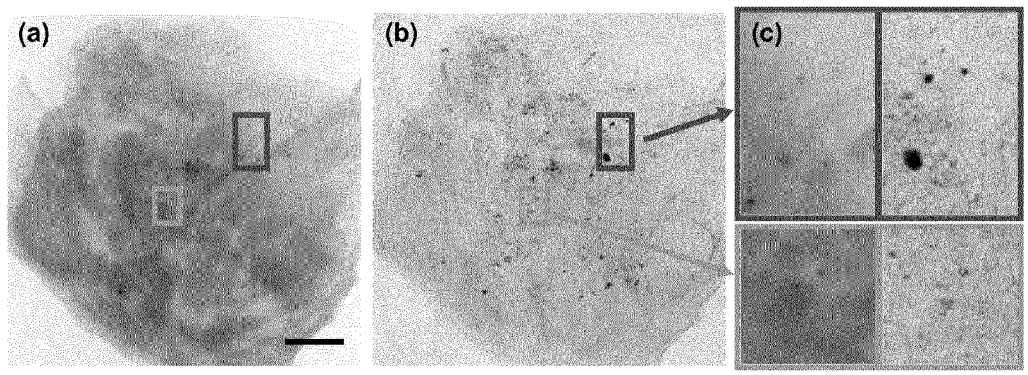
FIG. 1 shows a breast tissue sample that comprises two types of micro-calcifications having opposite absorption and small-angle scattering signals recorded by the grating interferometer.

With respect to the physical background, it is well known that the absorption of x-rays by single-material matter follows Beer's law, that is, $I = I_0 e^{-\mu t}$, where $\mu$ is the linear attenuation coefficient of the sample and t is the thickness of the sample. This is the fundamental principle of x-ray imaging used in conventional clinical apparatus.

More generally, for small and negligible anisotropy in the medium, the interaction between a tissue and x-rays can be expressed—including X-ray absorption—with its complex form: $n = 1 - \delta - i\beta$ where $\delta$ is the decrement of the real part of the refractive index, characterizing the phase shifting property, while the imaginary part β describes the absorption property of the sample. β is related to the x-ray linear attenuation coefficient μ by $$\beta = \frac{\lambda}{4\pi}\mu,$$

where λ is the wave length of the x-ray.

Additionally, any in-homogeneities in the micro- or nanometer range within the sample, such as the micro-calcifications considered as target substance in the context of the present invention, will cause x-ray photons to scatter. This forward scattering concentrates in very small angles, and therefore this phenomenon is called small-angle scattering. Measurements of the local small-angle scattering power can deliver important structural information about the sample, and are thus widely used in the characterization of materials.

In the following, the absorption contrast is noted by "AC" and the small-angle scattering contrast by "SC". In radiography, the AC signal is well-known as the line integration of the attenuation coefficients and the SC signal is directly proportional to the linear integration of the generalized scattering parameters:

$$AC = \int_0^L \mu(l)dl = \bar{\mu} \cdot L \qquad (1),$$

$$SC = c\int_0^L S(l)dl = c\bar{S} \cdot L \qquad (2),$$

where L is the thickness of the specimen, μ is the attenuation coefficient, S is the generalized scattering parameter and c is a constant decided by the geometry and system parameters of the imaging setup.

As mentioned previously, the most useful way to distinguish micro-calcification types is to do it non-invasively, at the breast imaging stage. This would be of greatest benefit to the diagnosis process and to patients.

With single modality x-ray imaging methods, e.g. current absorption-based mammography, it is not possible because chemical composition and structure information can not be obtained, only morphological information is available for analysis.

Additionally, conventional mammography bears the 2D limitation, namely that the thickness of the micro-calcifications cannot be determined from the mammograms. Therefore, although these two types of micro-calcification have different attenuation coefficients, they are still unable to be classified due to the unknown thickness.

The way to overcome this problem foresees according to the present invention to involve another physical quantity in order to decouple the thickness parameter. And ideally this quantity should be obtained with the absorption information simultaneously. This requirement will maximally reduce the errors due to imaging the specimen in different circumstances. The multiple-modality imaging system as proposed in this invention is the potential solution, such as the grating interferometer.

The difficulty of distinguishing type I and type II micro-calcifications in x-ray imaging is solved according to the present invention by involving the small-angle scattering signal. By taking the small-angle scattering signal as a complement to the absorption signal, this invention considers the differences of the attenuation coefficient as well as the crystal structure of these two most relevant types of micro-calcifications.

Generally speaking, type I and type II give opposite absorption and scattering signals. That is, one type gives a weaker absorption signal but a stronger small-angle scattering signal than the other type. The additional and complementary small-angle scattering signal helps to determine the type. An experimental observation is shown in FIG. 1.

Figure 2:
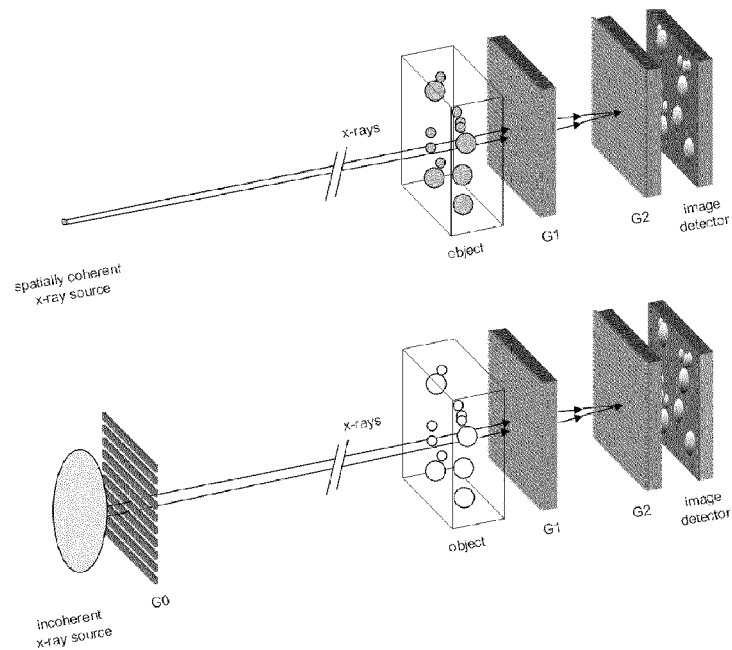
FIG. 2 illustrates schematically a two-gratings set-up (top) and a three-gratings set-up (bottom) for x-ray imaging.

FIG. 1 shows a breast tissue sample showing that two types of micro-calcifications have opposite absorption and small-angle scattering signals recorded by a grating interferometer as shown in FIG. 2. FIG. 1(a) depicts the absorption image of a breast specimen which contains micro-calcifications. FIG. 1(b) depicts the small-angle scattering image of the same specimen. FIG. 1(c) shows the details of the ROI located by the light grey and dark grey rectangulars in FIGS. 1(a) and 1(b). The micro-calcifications within the dark grey rectangular (right rectangular) have weaker absorption signals but stronger scattering signals; while those within the light grey rectangular (left rectangular) have relatively stronger absorption signals but weaker scattering signals.

In detail, based on the experimental observations, type I micro-calcifications have a smaller attenuation coefficient than type II. Due to the crystal structure of type I micro-calcifications, stronger refraction occurs when x-ray photons pass through them. This refraction will contribute to the small-angle scattering signal in image formation, for instance when using the grating interferometer as shown in FIG. 2. Therefore, generally type I gives a higher scattering signal than type II for the same thickness.

When having a closer look to the signal evaluation means which are a commodity workstation running a specific evaluation software, the evaluation benefits from the fact that there are two types of micro-calcifications and their absorption and small-angle scattering signals are opposite, eventually, their types are uniquely determined. As an example supposing that there are two micro-calcifications (A and B) which give opposite absorption and scattering signals. Without loss of generality, it is supposed $AC\_A < AC\_B$ and $SC\_A > SC\_B$, where AC represents the absorption signal and SC represents the small-angle scattering signal. The absorption signal can be generally expressed by Eq. (1). If $AC\_A < AC\_B$, there are two possible reasons:

Either they are the same type but the thickness of B is larger than A or they belong to different types of micro-calcification. These two possibilities can be narrowed down to one by the small-angle scattering signals. If it is the former case, one will get $T\_A < T\_B$ where T presents the thickness. According to the linear relationship of the small-angle scattering power with the thickness L in Eq. (2), it is not possible to have $SC\_A > SC\_B$. Consequentially, it can be determined that they belong to different types. Moreover, micro-calcification A more likely belongs to type I while micro-calcification B belongs to type II.

A signal pair $(t_1, t_2)$ can be assigned to each of two micro-calcifications. $t_1, t_2 \subset \{+,-\}$, $t_1$ and $t_2$ represent the relative signal strength of the absorption signals and the small angle scattering signals, respectively. "+" means this signal is stronger, "−" means this signal is weaker. If two signal pairs constitute a combination of (+,−) and (−,+), then they belong to different types. A micro-calcification signed to (−,+) is more likely to be type I whilst (+,−) indicates that this micro-calcification is more likely to be type II.

To decouple the thickness parameter, the ratio r of the absorption to the small-angle scattering can be obtained using Eq. (1) and Eq. (2), which is $$r = \frac{AC}{SC} \qquad (6)$$

$$= \frac{\bar{\mu} \cdot L}{c\bar{S} \cdot L}$$

$$= \frac{\bar{\mu}}{c\bar{S}}.$$

A threshold t is given, $$\begin{cases} r < t, \text{ one type} \\ r > t, \text{ another type} \end{cases} \quad (7)$$

This threshold t can be decided by experiments on known micro-calcifications in a statistical way. This threshold decided the sensitivity and specificity of the evaluation module comprised in the data processing means.

The present invention is also applicable to multiple-modality computed tomography. By reconstructing the tomograms of the absorption signal and the scattering signal from their projections, the average attenuation coefficient $\bar{\mu}$ and general scattering parameter $c\bar{S}$ can be obtained directly. These two signals are also opposite for the two types of micro-calcifications, so the same rule works.

In this invention, the absorption signals and the small-angle scattering signals obtained with multiple-modality systems are adopted to distinguish two types of micro-calcifications. Such multiple-modality systems have been developed in the last fifteen years, including techniques based on analyzer crystal, gratings and coded apertures. The described invention is therefore in context with these techniques.

Clinical applications demand techniques which can work well in a hospital environment. For this reason, grating-based methods are especially promising as they work well with conventional x-ray tubes. Without loss of generality, the practical aspects of the present invention will be discussed using gratings-based interferometry as an example.

Grating-based x-ray imaging setups can generate three different signals: the conventional absorption contrast (AC) signal, the differential phase contrast (DPC) signal caused by refraction due to phase shifts, and the small-angle scattering contrast (SC) signal (also named dark-field signal) caused by scattering from in-homogeneities in the sample.

Set-ups with two gratings G1 and G2 (FIG. 2a) or three gratings G0, G1, and G2 (FIG. 2b) can be applied to record the deflection of the x-rays. In the case of a two-grating set-up, the source needs to fulfill certain requirements regarding its spatial coherence, while in a three grating setup no spatial coherence is required. The grating G0 is required, when the X-ray source size is bigger than p2*l/d, where p2 is the period of the grating G2, l is the distance between the X-ray source and the grating G1, and d is the distance between the grating G1 and the grating G2. Therefore, the three grating set-up is suited for use with incoherent x-ray sources, in particular with x-ray tubes.

To separate the conventional attenuation contrast (AC) from the DPC and SC contrast, a phase-stepping approach is applied. One of the gratings is displaced transversely to the incident beam whilst acquiring multiple images. The intensity signal at each pixel in the detector plane oscillates as a function of the displacement. The average value of the oscillation represents the AC. The phase of the oscillation can be directly linked to the wave-front phase profile and thus to the DPC signal. The amplitude of the oscillation depends on the scattering of x-rays in the object and thus yields the SC signal.

For the (two or three) gratings, several approaches have been proposed and applied. The grating G0 (if required) is the one closest to the X-ray source. It usually consists of a transmission grating of absorbing lines with the period p0. It can be replaced by an X-ray source that emits radiation only from lines with the same period. The grating G1 is placed further downstream of the X-ray source. It consists of lines with a period p1. The grating G2 is the one most downstream of the setup. It usually consists of a transmission grating of absorbing lines with the period p2. It can be replaced by a detector system that has a grating-like sensitivity with the same period.

Two regimes of setups can be distinguished: in the so called "near field regime" and the "Talbot regime". A sharp distinction between the two regimes is not easily given, as the exact criterion depends on the duty cycle of the grating structure, and whether the gratings are absorbing or phase shifting. E.g., for a grating with absorbing lines and a duty cycle of 0.5, the condition for the "near field regime" is $d \geq p^2/2\lambda$.

In the "near field regime", the grating period p, grating distances d and the x-ray wavelength $\lambda$ are chosen such, that diffraction effects are negligible. In this case, all gratings need to consist of absorbing lines.

In the "Talbot regime", diffraction from the grating structures is significant. Here, the grating G1 should consist of grating lines that are either absorbing or, preferentially, phase shifting. Several amounts of phase shift are possible, preferentially $\pi/2$ or multiples thereof. The grating periods must be matched to the relative distances between the gratings. In the case of setups in the "Talbot regime" the Talbot effect needs to be taken into account to obtain good contrast. The formulae for the grating periods and distances are described in the literature.

The sample is mostly placed between the grating G0 and the grating G1 (or upstream of the grating G1 in the case of a two-grating set-up), however it can be advantageous to place it between the grating G1 and the grating G2.

The presented invention is relevant in all of the above-mentioned cases, i.e. in the two- and three-gratings case, in the case of the "near-field regime" and the "Talbot regime", and for the sample placed upstream or downstream of the grating G1.

In addition, the invention presented here also works in combination with scanning-based systems or for planar grating geometries.

Intensity curves (with and without sample) are usually obtained with "phase stepping" methods or alternative techniques. Defining for each pixel on the detector the mean, phase and visibility of the intensity curve with sample as $I_s$, $\Phi_s$, $V_s$, and without sample as $I_b$, $\Phi_b$, $V_b$, yields:

$$AC = -\log\left(\frac{I_s}{I_b}\right) \quad (3)$$

$$DPC = \Phi_s - \Phi_b \quad (4)$$

$$SC = -\log\left(\frac{V_s}{V_b}\right). \quad (5)$$

For both the AC signal and SC signal, the valid data range is $[0,+\infty]$, while for the DPC it is $[-\pi,+\pi]$. Images obtained by plotting such signals are all perfectly registered.

A similar way to generate these multiple information signals can be found in diffraction enhanced imaging where the equivalent of the intensity curve is named the rocking curve.

The invention claimed is:

1. A system for a non-invasive classification of different types of micro-calcifications in human tissue by combining an absorption signal and a small-angle scattering signal, the system comprising:
   a set-up for recording the absorption signal and the small-angle scattering signal; and
   signal processing means configured to analyze at least one pair of micro-calcifications, an analysis based on different types of micro-calcifications having opposite absorption and small angle scattering signals, wherein, one type gives a weaker absorption signal but a stronger small-angle scattering signal than the other type or vice-versa.

2. The system according to claim 1,
   wherein a signal pair $(t_1,t_2)$ is assigned to a pair of micro-calcifications, where $t_1,t_2 \subset \{+,-\}$ and $t_1$ and $t_2$ represent a relative signal strength of the absorption signal and the small angle scattering signal, respectively, wherein "+" means a signal is stronger, "−" means the signals is weaker; and
   further comprising an evaluator module disposed in said signal processing means for identifying if two signal pairs constitute a combination of (+,−) and (−,+), which yields that the two signal pairs belong to different types of micro-calcifications wherein a micro-calcification signed to (−,+) is determined to be more likely a type I micro-calcification whereas (+,−) indicates that the micro-calcification is determined to be more likely a type II micro-calcification.

3. The system according to claim 1, wherein said signal processing means calculates a ratio r of the absorption signal and the small-angle scattering signal of the micro-calcification to decouple a thickness parameter and identify micro-calcification types I and II, wherein $$r = \frac{AC}{SC}$$
$$= \frac{\bar{\mu} \cdot L}{c\bar{S} \cdot L}$$
$$= \frac{\bar{\mu}}{c\bar{S}},$$

where
AC is the absorption signal, $AC = \int_0^L \mu(l)dl = \bar{\mu} \cdot L$;
SC is the small-angle scattering signal, $SC = c\int_0^L S(l) dl = c\bar{S} \cdot L$;
L is a thickness of a specimen;
$\mu$ is an attenuation coefficient;
S is a generalized scattering parameter;
c is a constant decided by geometry and system parameters of said set-up; and
further using an predetermined threshold t that will sort out if, $$\begin{cases} r < t, & \text{one type of the micro-calcification} \\ r > t, & \text{another type of the micro-calcification} \end{cases}.$$

4. The system according to claim 3, wherein when signal data is obtained with multi-modality computed tomography, said signal processing means reconstructs tomograms of absorption information and small-angle scattering information from projection and the attenuation coefficient μ and the generalized scattering parameter S are obtained directly, wherein the absorption information and the small-angle scattering information are also opposite for two types of the micro-calcifications.

5. The system according to claim 1, wherein the absorption signal and small-angle scattering signal are obtained from a configuration outputting x-rays, for obtaining quantitative x-ray images from a sample, said configuration including:
   an X-ray source;
   said setup having at least two gratings;
   a position-sensitive detector with spatially modulated detection sensitivity having a number of individual pixels;
   means for recording images of said position-sensitive detector;
   said signal processing means having an evaluator module enabled to evaluate intensities for each pixel in a series of the images, in order to identify characteristics of an object for each individual pixel as an absorption dominated pixel, a differential phase contrast dominated pixel or an x-ray scattering dominated pixel; and
   wherein the series of the images is collected by continuously or stepwise rotating from 0 to π or 2π either a sample or said setup and said x-ray source relative to the sample.

6. The system according to claim 5, wherein the system performs in a so-called "near field regime" or in a "Talbot-regime".

7. The system according to claim 5, wherein said gratings include:
   a first line grating selected from the group consisting of absorption gratings and phase gratings and is a low absorption grating generating a considerable X-ray phase shift; and
   a second line grating having a high X-ray absorption contrast with its period being a same as that of a self image of said first line grating; and
   said second line grating is disposed closely in front of said position-sensitive detector with its lines parallel to those of said first line grating.

8. The system according to claim 7, wherein for near-field-regime operation, a distance between said gratings is chosen freely within the near field regime, and for the Talbot-regime is chosen according to $$D_{n,sph} = \frac{L \cdot D_n}{L - D_n}$$
$$= \frac{L \cdot n \cdot p_1^2 / 2\eta^2 \lambda}{L - n \cdot p_1^2 / 2\eta^2 \lambda}$$

where n=1,3,5 . . . , and $$\eta = \begin{cases} 1 & \text{if the phase shift of } G_1 \text{ is } (2l-1)\frac{\pi}{2}, \quad p_2 = \frac{L + D_{n,psh}}{L} p_1 \\ 2 & \text{if the phase shift of } G_1 \text{ is } (2l-1)\pi, \quad p_2 = \frac{L + D_{n,psh}}{L} \frac{p_1}{2} \end{cases}$$

where l=1,2,3 ..., $D_n$ is an odd fractional Talbot distance when a parallel X-ray beam is used, while $D_{n,sph}$ is that when a fan or cone X-ray beam is used, L is a distance between said x-ray source and said first line grating, and G1 is said first line grating.

9. The system according to claim 5, wherein said at least two gratings are two of three gratings, and phase stepping is performed by a shift of one of said three gratings with respect to said other gratings.

10. The system according to claim 1, wherein said set-up for recording the absorption signal and the small-angle scattering signal records signals of X-ray investigations based on grating-based interferometry, based on analyzer-crystal-based imaging or based on coded aperture imaging.

11. The system according to claim 5, wherein the absorption signal and the small-angle scattering signal are obtained from a configuration outputting hard x-rays.

12. The system according to claim 7, wherein the considerable X-ray phase shift being of $\pi$ or odd multiples thereof.

* * * * *